United States Patent
Asafusa et al.

(10) Patent No.: US 8,579,823 B2
(45) Date of Patent: Nov. 12, 2013

(54) ULTRASONIC DIAGNOSTIC APPARATUS AND ULTRASONIC PROBE USED IN SAME

(75) Inventors: Katsunori Asafusa, Tokyo (JP); Kousuke Kanbara, Tokyo (JP); Kenji Maio, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 51 days.

(21) Appl. No.: 13/377,272

(22) PCT Filed: Jun. 7, 2010

(86) PCT No.: PCT/JP2010/059609
§ 371 (c)(1),
(2), (4) Date: Dec. 9, 2011

(87) PCT Pub. No.: WO2010/143604
PCT Pub. Date: Dec. 16, 2010

(65) Prior Publication Data
US 2012/0078112 A1    Mar. 29, 2012

(30) Foreign Application Priority Data
Jun. 12, 2009    (JP) ................................ 2009-140704

(51) Int. Cl.
*A61B 8/14*    (2006.01)

(52) U.S. Cl.
USPC .......................................................... 600/459

(58) Field of Classification Search
USPC ................ 600/437, 459, 462; 73/632; 367/87
See application file for complete search history.

(56) References Cited

FOREIGN PATENT DOCUMENTS

| JP | 63-177389 | 7/1988 |
|---|---|---|
| JP | 9-033638 | 2/1997 |
| JP | 2006-68090 | 3/2006 |
| JP | 2007-319286 | 12/2007 |

*Primary Examiner* — Michael Rozanski
(74) *Attorney, Agent, or Firm* — Brundidge & Stanger, P.C.

(57) ABSTRACT

The present invention provides an ultrasonic probe contains at least one reception preamplifier that is provided per transducer element and connected to the transducer at an input side thereof and to a cable at an output side thereof, a transmission bypass unit that is connected between the cable and the transducer, blocks off a reception signal and allows a transmission signal to pass therethrough, and a floating unit that is connected between a power supply terminal of the preamplifier and a driving power source and increases impedance thereof for a high-voltage transmission signal, whereby a bias potential of the preamplifier is electrically set to a floating state and returned to an original bias potential by a reception time.

8 Claims, 7 Drawing Sheets

FIG. 7

ULTRASONIC DIAGNOSTIC APPARATUS AND ULTRASONIC PROBE USED IN SAME

TECHNICAL FIELD

The present invention relates to an ultrasonic diagnostic apparatus in which an ultrasonic probe containing at least one transducer and a transceiver containing a transmission amplifier and a reception circuit are connected to each other through a cable, and an ultrasonic probe used in the same.

BACKGROUND ART

In general, the ultrasonic diagnostic apparatus contains a transmission circuit for generating a high voltage AC signal in the device, and a high-voltage transmission pulse is transmitted through a cable to excite the ultrasonic transducer in an ultrasonic probe. Furthermore, an ultrasonic wave reflected and returned from a living body is received by the ultrasonic transducer, and a reception signal is likewise transmitted through the cable into the device, separated in a TR separation circuit (transmission/reception separating circuit), transmitted to the reception circuit to be amplified, and then transmitted to an image processor.

The reception signal is generally a very faint signal of about several tens to several hundreds mV. Accordingly, these signals are lowered in signal level due to voltage division caused by parasitic capacitance of the cable, or SNR remarkably deteriorates due to a cable insertion loss or an effect of parasitic resistance of a high-voltage switch. Therefore, it is considered that a preamplifier is provided to a grip end portion in the ultrasonic probe (probe) to amplify a reception signal when the reception signal is transmitted through the cable, whereby an effect of noise can be relatively suppressed.

Patent Document 1 is known as a circuit which has been hitherto devised to provide a preamplifier in an ultrasonic probe.

Furthermore, Patent Document 2 is also an example of a circuit for protecting a preamplifier.

PRIOR ART DOCUMENT

Patent Document

Patent Document 1: JP-A-63-177389
Patent Document 2: JP-A-2007-319286

SUMMARY OF THE INVENTION

Problem to be solved by the Invention

However, when the preamplifier mounted in the grip end portion in the ultrasonic probe, the grip end portion is a site which is directly handled by an operator, and thus usability is greatly affected by the shape and weight of the grip end portion. Accordingly, it is very important that the circuit is small in scale and light in weight when it is mounted in the grip end portion. Accordingly, there is required a simple circuit construction which does not use any transmission/reception separating circuit as much as possible and does not require opening/closing control.

The invention has been implemented in view of these problems, and has an object to provide a compact and light ultrasonic probe that prevents increase of transmission functionality, reception functionality and an attendant circuit thereto in circuit scale, an ultrasonic diagnostic apparatus using the ultrasonic probe, and an ultrasonic probe used in the ultrasonic diagnostic apparatus.

Means of Solving the Problem

In order to solve the above problem, according to the invention, in an ultrasonic diagnostic apparatus having an ultrasonic probe containing at least one transducer therein and a transceiver containing a transmission amplifier and a reception circuit therein which are used in connection with each other through a cable, the ultrasonic probe contains:

at least one reception preamplifier that is provided per transducer element and connected to the transducer at an input side thereof and to a cable at an output side thereof;

a transmission bypass unit that is connected between the cable and the transducer, blocks off a reception signal and allows a transmission signal to pass therethrough; and a floating unit that is connected between a power supply terminal of the preamplifier and a driving power source and increases impedance thereof for a high-voltage transmission signal, whereby a bias potential of the preamplifier is electrically set to a floating state and returned to an original bias potential by a reception time.

In the invention, the floating unit may be constructed by a backflow preventing diode connected between the power supply terminal of the preamplifier and the driving power source, and a capacitor connected to the diode.

In the invention, the transmission bypass unit may be constructed by diodes which are connected to each other in a back-to-back connection style.

In the invention, the reception preamplifier may be constructed by an emitter follower circuit based on transistors, or a source follower circuit based on FET.

Furthermore, according to the invention, in an ultrasonic diagnostic apparatus having an ultrasonic probe containing at least one transducer therein and a transceiver containing a transmission amplifier and a reception circuit therein which are used in connection with each other through a cable, the ultrasonic probe contains:

at least one reception preamplifier that is provided per transducer element and connected to the transducer at an input side thereof and to a cable at an output side thereof; and a floating unit that is connected between a power supply terminal of the preamplifier and a driving power source and increases impedance thereof for a high-voltage transmission signal, whereby a bias potential of the preamplifier is electrically set to a floating state and returned to an original bias potential by a reception time, wherein the reception preamplifier allows a transmission signal to pass from a cable side to a transducer side under the floating state.

In the invention, the floating unit may be constructed by a backflow preventing diode connected between the power supply terminal of the preamplifier and the driving power source, and a capacitor connected to the diode.

In the invention, the reception amplifier may be constructed by an emitter follower circuit based on high withstanding voltage transistors, or an emitter follower circuit in which a PNP transistor and an NPN transistor are connected to each other in series so that emitters thereof are commonly connected to each other.

Still furthermore, according to the invention, in an ultrasonic probe having at least one transducer contained in a case, the case contains:

at least one reception preamplifier that is provided per transducer element and connected to the transducer at an input side thereof and to a cable at an output side thereof;

a transmission bypass unit that is connected between the cable and the transducer, blocks off a reception signal and allows a transmission signal to pass therethrough; and a floating unit that is connected between a power supply terminal of the preamplifier and a driving power source and increases impedance thereof for a high-voltage transmission signal, whereby a bias potential of the preamplifier is electrically set to a floating state and returned to an original bias potential by a reception time.

In the invention, the floating unit may be constructed by a backflow preventing diode connected between the power supply terminal of the preamplifier and the driving power source, and a capacitor connected to the diode.

Still furthermore, according to the invention, in an ultrasonic probe having at least one transducer in a case, the case contains at least one reception preamplifier that is provided per transducer element and connected to the transducer at an input side thereof and to a cable at an output side thereof, and a floating unit that is connected between a power supply terminal of the preamplifier and a driving power source and increases impedance thereof for a high-voltage transmission signal, whereby a bias potential of the preamplifier is electrically set to a floating state and returned to an original bias potential by a reception time, and the reception preamplifier allows a transmission signal to pass from a cable side to a transducer side under the floating state.

In the invention, the floating unit may be constructed by a backflow preventing diode connected between the power supply terminal of the preamplifier and the driving power source, and a capacitor connected to the diode.

In the invention, the reception amplifier may be constructed by an emitter follower circuit based on high withstanding voltage transistors.

Effect of the Invention

According to the invention, the reception amplifier is installed in the ultrasonic probe without increasing the transmission functionality, the reception functionality and the appendant circuit thereto, and thus the compact and light ultrasonic probe and the ultrasonic diagnostic apparatus using the ultrasonic probe can be provided.

MODES FOR CARRYING OUT THE INVENTION

Embodiments of an ultrasonic diagnostic apparatus according to the invention will be described in detail with reference to the drawings. In the following description and drawings, the same constituent elements are represented by the same reference numerals and the duplicative description thereof is omitted.

Embodiment 1

Figure 1:
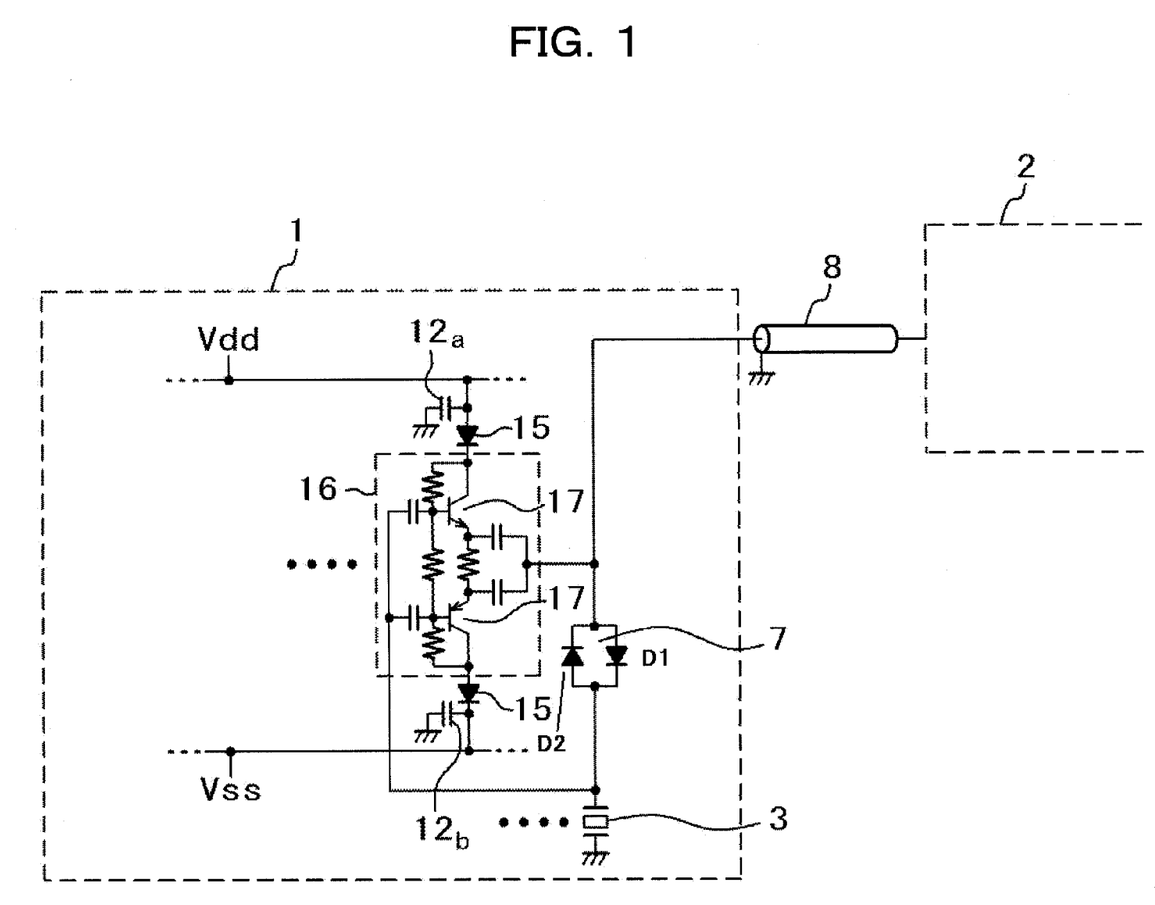
FIG. 1 is an electrical connection diagram showing a first embodiment of the invention.
Figure 2:
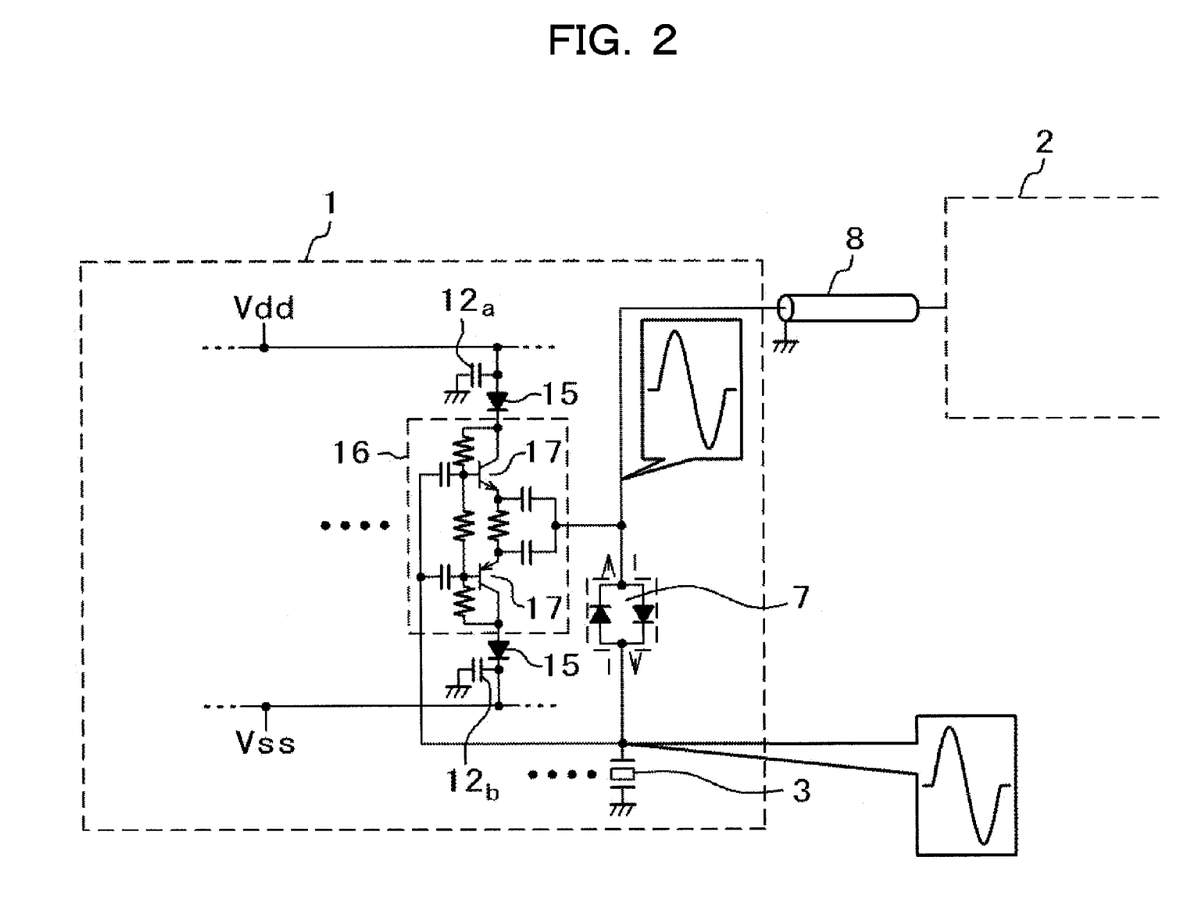
FIG. 2 is a diagram showing an operation of the first embodiment during transmission.
Figure 3:
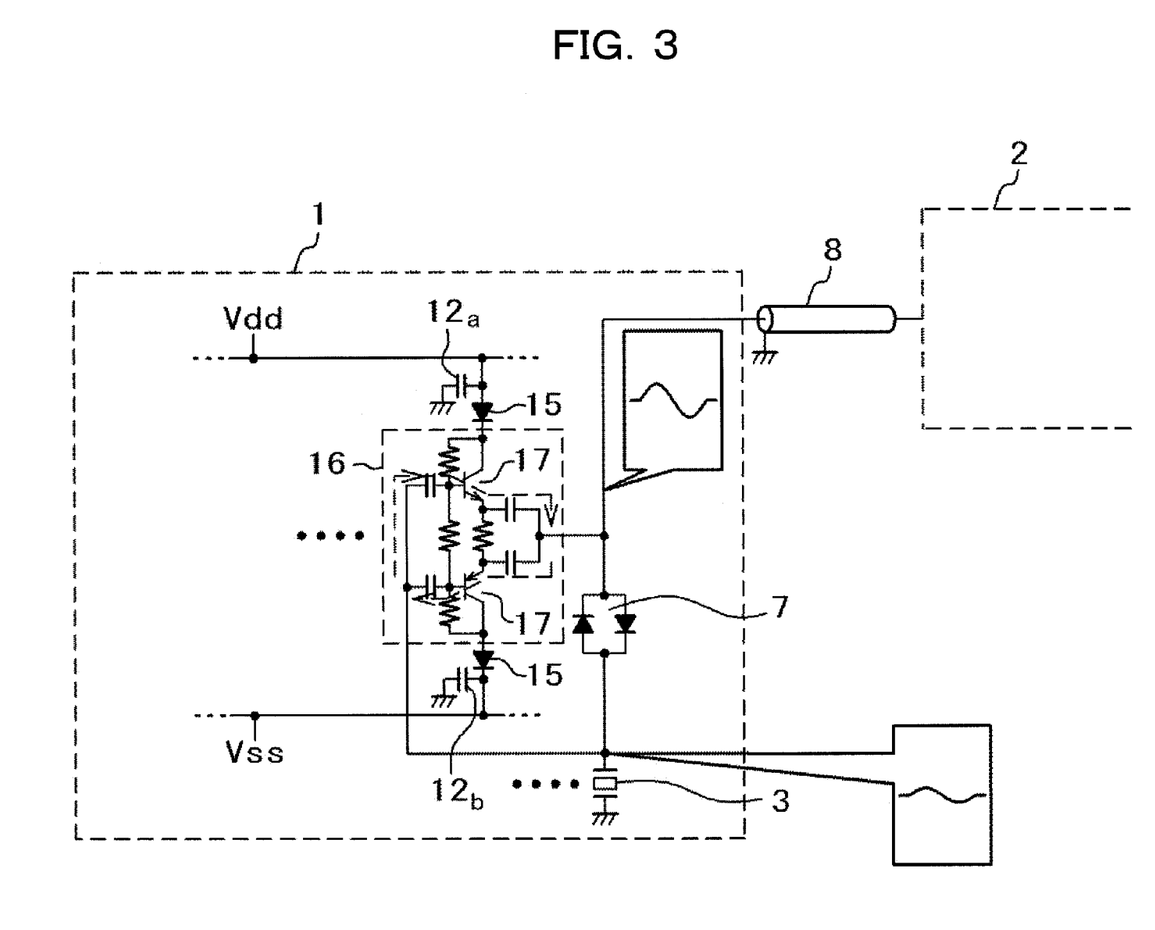
FIG. 3 is a diagram showing an operation of the first embodiment during reception.

FIG. 1 is an electrical connection diagram showing the first embodiment of the invention, and FIGS. 2 and 3 are diagrams showing an operation during transmission and an operation during reception in the first embodiment of the invention.

As shown in FIG. 1, an example of a buffer amplifier implemented by an emitter follower circuit 16 having two transistors is shown as a preamplifier for amplifying a reception signal.

An NPN type transistor 17 and a PNP type transistor 17 are connected to each other in series so that the emitters thereof serve as a common connection point, thereby constructing the emitter follower circuit 16. The input side of the emitter follower circuit 16 is connected to a transducer 3, and the output side thereof is connected to a cable 8. In this embodiment, the emitter follower circuit using the transistors is used as a preamplifier for reception, however, the reception preamplifier may be constructed by a source follower circuit using FET (electric field effect transistor).

Current is supplied from driving power sources Vdd and Vss through backflow preventing diodes 15 to the power supply terminal of the preamplifier concerned. A capacitor 12a, 12b is connected to the earth in the neighborhood of the connection point between the driving power source Vdd, Vss and the diode 15. The input side of the preamplifier is connected to the transducer 3, and the output side thereof is connected to the cable 8. A back-to-back connection diode 7 constructed by diodes D1 and D2 which are connected to each other in inverse-parallel connection style is connected between the transducer 3 and the cable 8.

A shown in FIG. 2, during transmission, a high-voltage transmission pulse excites the transducer 3 through the back-to-back connection diode 7 which prevents transmission of faint reception signal and allows only a high-voltage transmission pulse to pass therethrough. The back-to-back connection diode 7 corresponds to a transmission bypass unit of the invention.

A high-voltage transmission pulse is applied to the input terminal and output terminal of the preamplifier. However, as described above, the power supply terminal is set to an electrically floating state by the backflow preventing diodes 15, so that the bias potential of the preamplifier itself varies together with the voltage of the transmission pulse and thus no potential difference occurs, thereby performing a function of protecting the preamplifier. That is, a voltage of about ±5 to 100V is used as the transmission pulse, and a voltage of about ±2 to 5V is used as the voltages Vdd and Vss of the driving power sources. When the transmission pulse has a positive voltage, the diode 15 at the positive power source Vdd side is inversely biased and thus set to a block-off state. When the transmission pulse has a negative voltage, the diode 15 at the negative power source Vss side is inversely biased and thus set to a block-off state, so that the preamplifier is set to a floating state. Here, the voltage corresponding to the difference between the transmission pulse and the voltage Vdd, Vss of the driving power source is applied to the diode 15, and thus the diodes are required to have a high withstanding voltage.

Furthermore, as shown in FIG. 3, under reception, the bias potential of the preamplifier itself is returned to an original state, and the reception signal as a faint AC signal which is prevented by the back-to-back connection diode 7 is led to the preamplifier to be amplified at a predetermined gain. Here, capacitors 12 have an effect of supplying rapid current for recovery of the bias potential of the preamplifier from the transmission time to the reception time, and also suppressing rapid variation of a power supply voltage caused by an effect of a common impedance of the driving power sources Vdd and Vss. Furthermore, it is needless to say that the capacitors 12 also act as bypass capacitors when the reception signal is amplified. That is, when plural transducers and a reception preamplifier are provided, wraparound of a signal through a power supply circuit can be prevented by grounding through the capacitors 12. Here, the diodes 15 and the capacitors 12 correspond to a floating unit of the invention.

As described above, the merit of this embodiment resides in that the preamplifier can be installed in the ultrasonic probe with providing neither a special TR separating circuit nor an analog switch or without controlling them, and thus the circuit can be provided with a simple construction.

Embodiment 2

Figure 4:
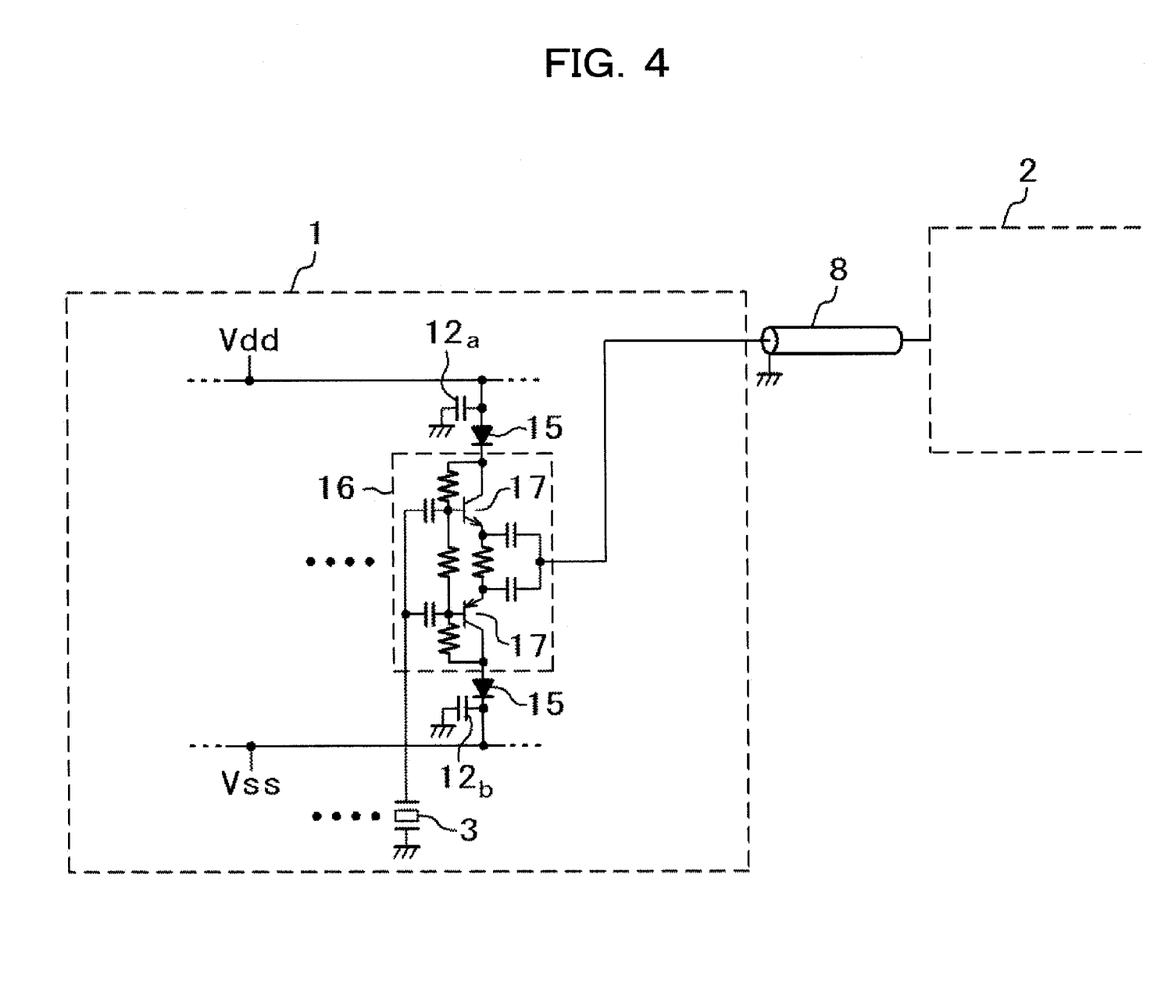
FIG. 4 is an electrical connection diagram showing a second embodiment of the invention.
Figure 5:
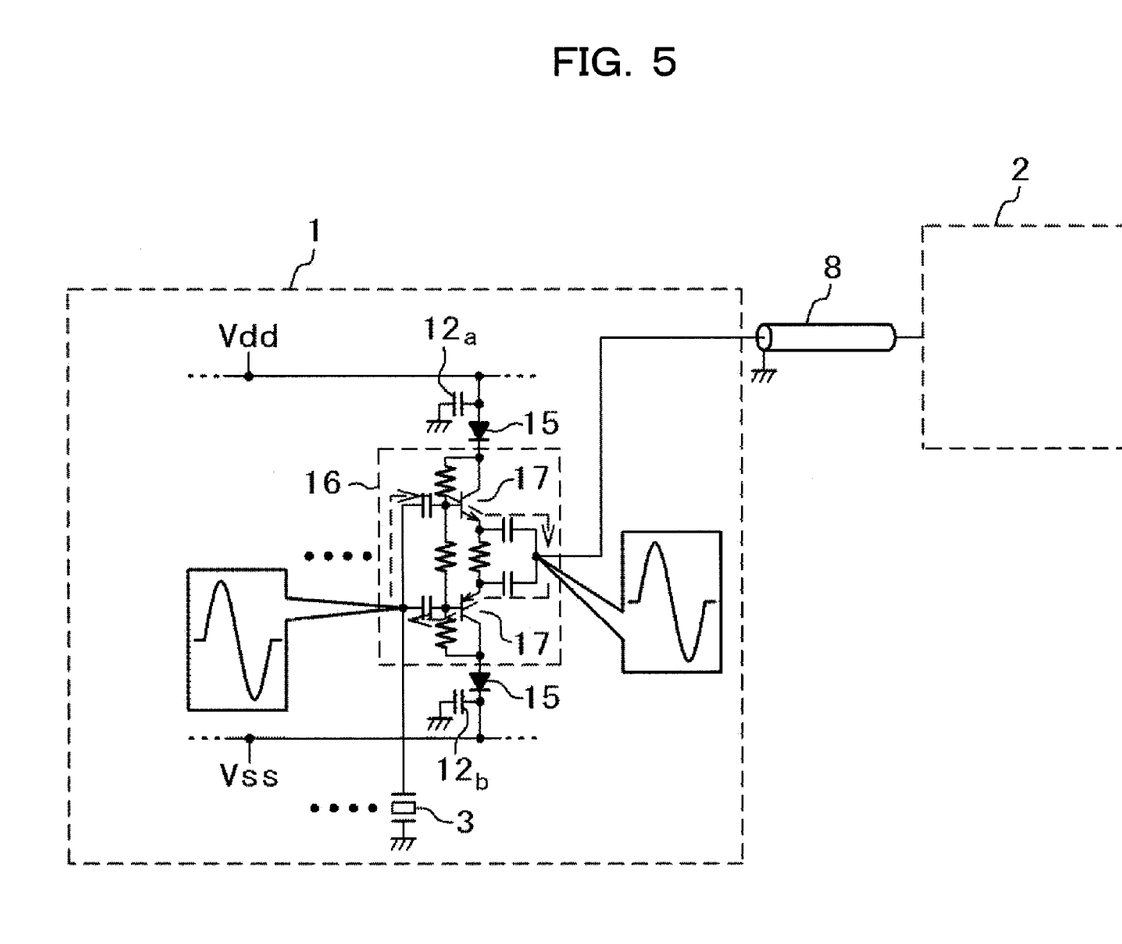
FIG. 5 is a diagram showing an operation of the second embodiment during transmission.
Figure 6:
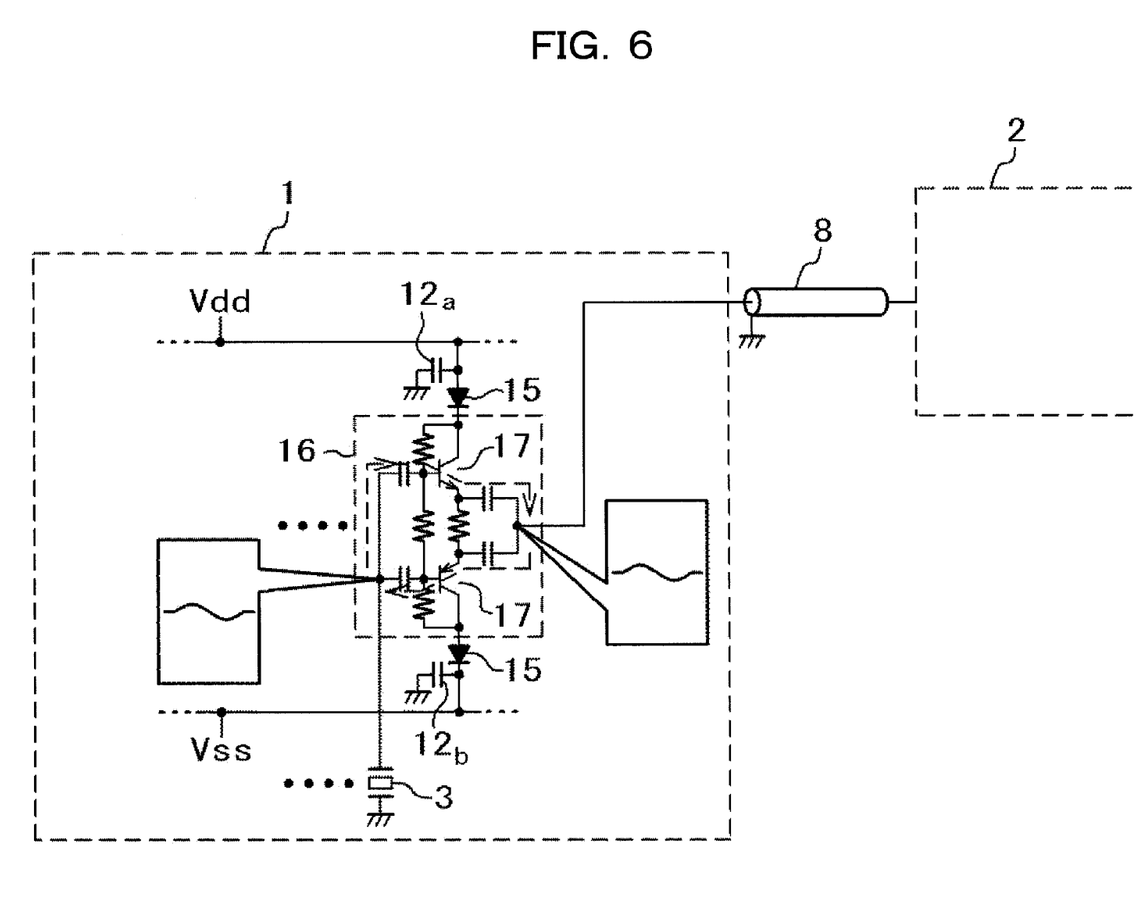
FIG. 6 is a diagram showing an operation of the second embodiment during reception.

FIG. 4 is an electrical connection diagram showing a second embodiment according to the invention, and FIGS. 5 and 6 are diagrams showing the operation of the second embodiment of the invention under transmission and under reception.

As shown in FIG. 4, an emitter follower circuit 16 for buffering a reception signal supplies current from driving power sources Vdd and Vss through backflow preventing diodes 15 to the power supply terminal of the emitter follower circuit. Furthermore, a capacitor 12a, 12b is connected between the earth and a neighborhood of the connection point of the driving source Vdd, Vss and the diode 15. Here, the diodes 15 and the capacitors 12 correspond to the floating unit of the invention.

In this embodiment, the emitter follower circuit 16 is constructed by connecting an NPN type high withstanding voltage transistor 17 and a PNP type high withstanding voltage transistor 17 in series while the emitters thereof serve as a common connection point. The input side of the emitter follower circuit 16 is connected to a transducer 3, and the output side thereof is connected to a cable 8.

A feature of the construction of this embodiment resides in that it is constructed by the emitter follower circuit 16 using the high withstanding voltage transistors, and another feature resides in that there is not used the back-to-back connection diode 7 which is provided in the embodiment 1 to prevent a faint reception signal and thus allow only a high voltage transmission pulse to pass therethrough and is constructed by the diodes D1 and D2 which are connected to each other in inverse-parallel connection style.

Under transmission, as shown in FIG. 5, the site between the base and the emitter of the two transistors 17 of the emitter follower operates as a diode. Specifically, when the high voltage transmission pulse has a positive voltage, AC current passes from the emitter of the PNP transistor through the base. When the high voltage transmission pulse has a negative voltage, AC current passes from the base of the NPN transistor through the emitter. The transducer 3 is excited through the emitter follower circuit 16. The high voltage transmission pulse is applied to the base and emitter terminals of the emitter follower circuit 16. However, as described above, the power supply terminals are set to the electrically floating state by the backflow preventing diodes 15, so that the bias potential of the preamplifier itself varies together with the voltage of the transmission pulse, and thus no potential difference occurs. A high voltage is applied between the collector and the base and between the collector and the emitter, and thus the transistors are required to be high withstanding voltage transistors.

Under reception, as shown in FIG. 6, the bias potential is recovered to the bias potential of the normal emitter follower, and the reception signal is buffered by the operation of the general emitter follower.

An example in which decoupling is performed by only the capacitors 12 is described above. However, a decoupling effect can be enhanced by arranging a resistor of about several $\Omega$ to several hundreds $\Omega$, a coil or ferrite in series between the driving power sources and the backflow preventing diodes 15.

With respect to a recovery time of the bias potential of the preamplifier from the floating state, it is desired that the bias potential is recovered by the reception time. Therefore, for example, the values of the capacitors at the base side and emitter side of the transistors of the emitter follower circuit may be determined on the basis of a time constant $\tau$ which is converged when the bias potential is recovered. Furthermore, as in the case of the embodiment 1, the capacitor 12 also serves as a bypass capacitor for the reception signal.

In addition to the merit of the embodiment 1, the merit of this embodiment as described above resides in that it is unnecessary to provide the back-to-back connection diode 7 and thus the circuit scale can be further reduced.

Accordingly, when the preamplifier is mounted in the grip end portion in the ultrasonic probe, a smaller and lighter ultrasonic probe can be implemented in comparison with prior arts.

Embodiment 3

Figure 7:
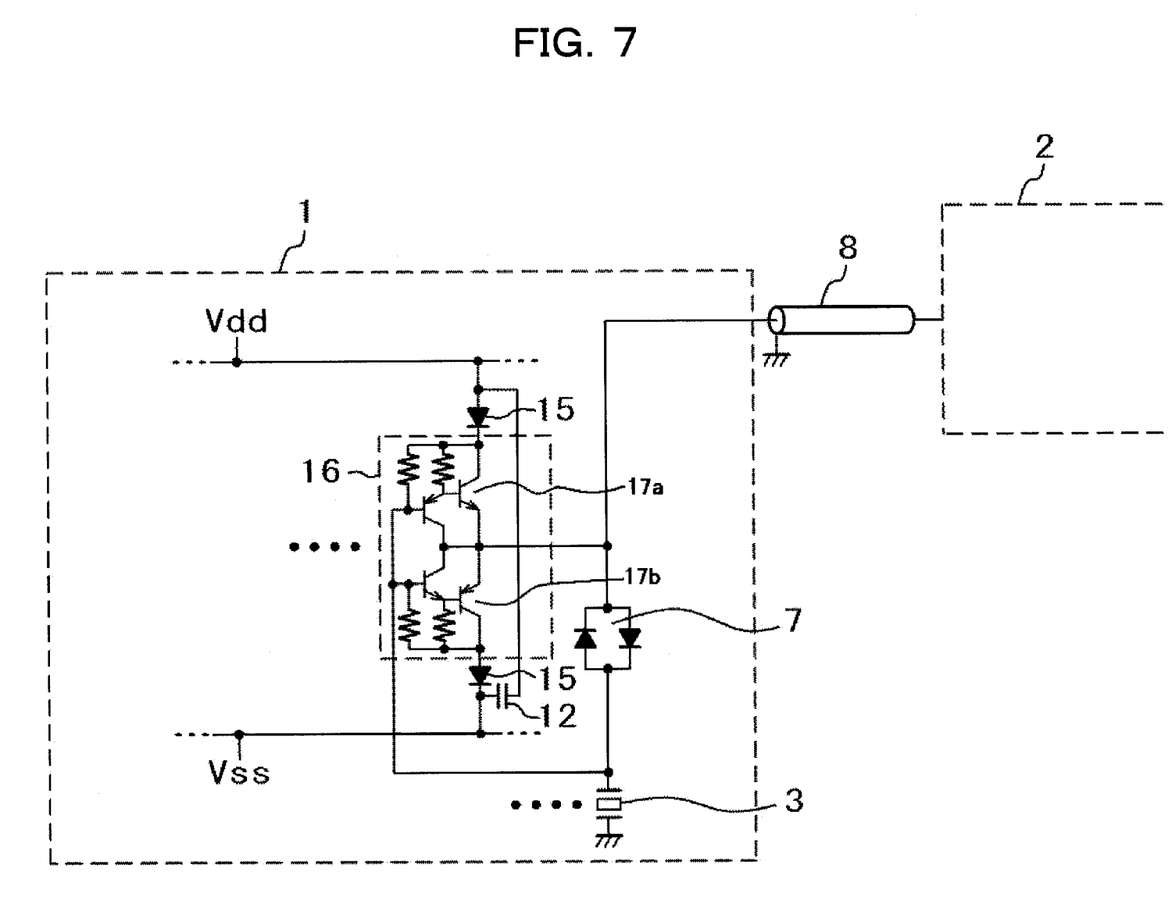
FIG. 7 is an electrical connection diagram showing a third embodiment of the invention.

FIG. 7 is an electrical connection diagram of the third embodiment of the invention.

An example in which a buffer amplifier is implemented as a preamplifier for amplifying a reception signal by an emitter follower circuit 16 of four transistors is shown in FIG. 7.

A first PNP type transistor 17a and a first NPN type transistor 17b are connected to each other in series so that the collectors thereof serve as a common connection point and also the bases thereof serve as a common connection point. In addition, the emitter of the first PNP type transistor 17a is connected to the base of a second NPN type transistor 17d, and the emitter of the first NPN type transistor 17b is connected to the base of a second PNP type transistor 17c. Furthermore, the second PNP type transistor 17d and the second PNP type transistor 17c are connected to each other in series so that the emitters thereof serve as a common connection point, whereby an emitter follower circuit 16 is constructed. The input side of the emitter follower circuit 16 is connected to the transducer 3, and the output side thereof is connected to a cable 8.

In this embodiment, the emitter follower circuit using the transistors is shown as the preamplifier for reception. However, it may be constructed by a source follower circuit using FET (electric field effect transistor).

The feature of the circuit construction of the third embodiment according to the invention resides in that the input and output of the preamplifier can be DC-coupled. Accordingly, no capacitor for AC coupling is required, and thus the circuit can be easily designed as an IC.

The operation of the circuit under transmission/reception is the same as the operations under transmission and under reception in the first embodiment according to the invention.

Particularly, an ultrasonic probe which exercises an electrical performance effect of the invention is an ultrasonic probe in which the impedance of the transducer 3 is equal to or more than the characteristic impedance of the cable, for example, 100Ω. Specifically, with respect to transducers such as a non-laminated PZT transducer (containing composite), a monocrystal transducer, cMUT, 2D array probe, the impedance of the transducer 3 is equal to about several hundreds Ω to several thousands Ω, the signal level is lowered due to voltage division caused by the parasitic capacitance of the cable 8, and SNR is remarkably deteriorated due to insertion loss of the cable and an effect of parasitic resistance of the high-voltage switch. When the invention is applied, the circuit is hardly affected by the parasitic impedance of the cable or the like due to signal amplification and lowering of the amplifier output impedance, so that the reduction of the reception signal level and the deterioration of SNR can be prevented.

DESCRIPTION OF REFERENCE NUMERALS 1 ultrasonic probe, 2 transceiver, 3 transducer, 7 back-to-back connection diode, 8 cable, 12, 12a, 12b capacitor, 15 diode, 16 emitter follower circuit, 17 transistor

The invention claimed is:

1. An ultrasonic diagnostic apparatus comprising:
an ultrasonic probe containing at least one transducer therein; and
a transceiver containing a transmission amplifier and a reception circuit therein,
wherein the ultrasonic probe and the transceiver are used in connection with each other through a cable, and
wherein the ultrasonic probe comprises:
at least one reception preamplifier that is provided per transducer element and connected to the transducer at an input side thereof and to a cable at an output side thereof;
a transmission bypass unit that is connected between the cable and the transducer, blocks off a reception signal and allows a transmission signal to pass therethrough; and
a floating unit that is connected between a power supply terminal of the reception preamplifier and a driving power source and increases impedance thereof for a high-voltage transmission signal, whereby a bias potential of the reception preamplifier is electrically set to a floating state and returned to an original bias potential by a reception time,
wherein the floating unit is constructed by a backflow preventing diode connected between the power supply terminal of the preamplifier and the driving power source, and a capacitor connected to the diode.

2. The ultrasonic diagnostic apparatus according to claim 1, wherein the transmission bypass unit is constructed by diodes which are connected to each other in a back-to-back connection style.

3. The ultrasonic diagnostic apparatus according to claim 1, wherein the reception preamplifier is constructed by an emitter follower circuit based on transistors.

4. The ultrasonic diagnostic apparatus according to claim 1, wherein the reception amplifier is constructed by a source follower circuit based on FET.

5. An ultrasonic diagnostic apparatus comprising:
an ultrasonic probe containing at least one transducer therein; and
a transceiver containing a transmission amplifier and a reception circuit therein,
wherein the ultrasonic probe and the transceiver are used in connection with each other through a cable, and
wherein the ultrasonic probe comprises:
at least one reception preamplifier that is provided per transducer element and connected to the transducer at an input side thereof and to a cable at an output side thereof; and
a floating unit that is connected between a power supply terminal of the preamplifier and a driving power source and increases impedance thereof for a high-voltage transmission signal, whereby a bias potential of the preamplifier is electrically set to a floating state and returned to an original bias potential by a reception time,
wherein the reception preamplifier allows a transmission signal to pass from a cable side to a transducer side under the floating state,
wherein the floating unit is constructed by a backflow preventing diode connected between the power supply terminal of the preamplifier and the driving power source, and a capacitor connected to the diode.

6. The ultrasonic diagnostic apparatus according to claim 5, wherein the reception amplifier is constructed by an emitter follower circuit based on high withstanding voltage transistors.

7. The ultrasonic diagnostic apparatus according to claim 6, wherein the emitter follower circuit is constructed by an emitter follower circuit in which a PNP transistor and an NPN transistor are connected to each other in series so that emitters thereof are commonly connected to each other.

8. An ultrasonic probe comprising:
at least one transducer contained in a case,
wherein the case comprises:
at least one reception preamplifier that is provided per transducer element and connected to the transducer at an input side thereof and to a cable at an output side thereof;
a transmission bypass unit that is connected between the cable and the transducer, blocks off a reception signal, and allows a transmission signal to pass therethrough; and
a floating unit that is connected between a power supply terminal of the reception preamplifier and a driving power source and increases impedance thereof for a high-voltage transmission signal, whereby a bias potential of the reception preamplifier is electrically set to a floating state and returned to an original bias potential by a reception time,
wherein the floating unit is constructed by a backflow preventing diode connected between the power supply terminal of the preamplifier and the driving power source, and a capacitor connected to the diode.

* * * * *